(12) United States Patent
Greene

(10) Patent No.: US 8,131,352 B2
(45) Date of Patent: Mar. 6, 2012

(54) SYSTEM AND METHOD FOR AUTOMATICALLY ADJUSTING DETECTION THRESHOLDS IN A FEEDBACK-CONTROLLED NEUROLOGICAL EVENT DETECTOR

(75) Inventor: David A. Greene, Fort Wayne, IN (US)

(73) Assignee: NeuroPace, Inc., Mountain View, CA (US)

( * ) Notice: Subject to any disclaimer, the term of this patent is extended or adjusted under 35 U.S.C. 154(b) by 1176 days.

(21) Appl. No.: 11/765,574

(22) Filed: Jun. 20, 2007

(65) Prior Publication Data

US 2008/0319335 A1 Dec. 25, 2008

(51) Int. Cl.
*A61B 5/04* (2006.01)
(52) U.S. Cl. .................................. 600/544; 600/545
(58) Field of Classification Search ............ 600/544, 600/378, 545; 607/45
See application file for complete search history.

(56) References Cited

U.S. PATENT DOCUMENTS

| | | | |
|---|---|---|---|
| 4,114,628 A | 9/1978 | Rizk | |
| 4,884,576 A | 12/1989 | Alt | |
| 4,940,052 A | 7/1990 | Mann et al. | |
| 5,324,310 A | 6/1994 | Greeninger et al. | |
| 5,413,592 A | 5/1995 | Schroeppel | |
| 5,913,880 A | 6/1999 | Vonk | |
| 6,016,449 A | 1/2000 | Fischell et al. | |
| 6,066,163 A | 5/2000 | John | |
| 6,366,813 B1 | 4/2002 | DiLorenzo | |
| 6,459,936 B2 | 10/2002 | Fischell et al. | |
| 6,463,328 B1 | 10/2002 | John | |
| 6,466,822 B1 | 10/2002 | Pless | |
| 6,473,639 B1 | 10/2002 | Fischell et al. | |
| 6,480,743 B1 | 11/2002 | Kirkpatrick et al. | |
| 6,594,524 B2 | 7/2003 | Esteller et al. | |
| 6,647,296 B2 | 11/2003 | Fischell et al. | |
| 6,810,285 B2 * | 10/2004 | Pless et al. | 600/544 |
| 6,944,501 B1 | 9/2005 | Pless | |
| 7,146,218 B2 | 12/2006 | Esteller et al. | |
| 7,149,572 B2 | 12/2006 | Frei et al. | |
| 7,181,283 B2 | 2/2007 | Hettrick et al. | |
| 2003/0073917 A1 * | 4/2003 | Echauz et al. | 600/510 |
| 2006/0276853 A1 | 12/2006 | Tass et al. | |
| 2007/0100378 A1 | 5/2007 | Maschino | |

OTHER PUBLICATIONS

Wirtzfeld et al, Central venous oxygen saturation for the control of automatic rate-responsive pacing, 1982, Pacing Clin. Electrophysiology 5(6):829-835.
Gentzler et al., Automatic Sensor Adjustment in a Rate Modulated Pacemaker, 1996, Pacing and Clinical Electrophysiology 19(11):1809-1812.
Benditt et al., Multiple-Sensor Systems for Physiologic Cardiac Pacing, 1994, Annals of Internal Med. 121(12):960-968.
Guyton, Textbook of Medical Physiology 659, 8$^{th}$ ed., W.B. Saunders Company, Philadelphia, 1991 (TOC).
Gotman, Automatic Seizure Detection: Improvements and Evaluation, 1990, Electroencephalogr. Clin. Neurophysiol. 76(4):317-324.
U.S. Appl. No. 60/095,413, filed Aug. 5, 1998.

* cited by examiner

*Primary Examiner* — Patricia Mallari
*Assistant Examiner* — Tiffany Weston

(57) ABSTRACT

Methods and systems for detecting neurological events and approximating a target detection rate are disclosed. A target detection rate may be identified for the neurological event. Electrographic signals incident on a neurological event detector may be monitored. Each signal may be compared to a threshold value for a parameter. As the threshold value varies, it has a predictable effect on a detection rate of the neurological event. A rate at which the electrographic signals exceed the threshold value may be measured and compared to the target detection rate. The threshold value may be adjusted to minimize the difference between the measured detection rate and the target detection rate.

24 Claims, 10 Drawing Sheets

SYSTEM AND METHOD FOR AUTOMATICALLY ADJUSTING DETECTION THRESHOLDS IN A FEEDBACK-CONTROLLED NEUROLOGICAL EVENT DETECTOR

BACKGROUND

1. Technical Field

The disclosed embodiments generally relate to neurological event detector systems, devices and methods that are configured to detect the occurrence of an event or condition of interest in a patient. More particularly, the disclosed embodiments relate to systems and methods for automatically adjusting the threshold at or above which an event or condition is detected based on the difference between a target detection rate and an actual or measured detection rate associated with the event or conditions.

2. Background

Neurostimulation systems, and increasingly implantable neurostimulation systems, are being used for the treatment of various chronic diseases and neurological disorders, such as pain management, epilepsy, and movement disorders such as Parkinson's disease. Research is ongoing concerning the application of implantable neurostimulation systems for treatment of psychological disorders, headaches, and for stroke recovery and Alzheimer's disease. Other disorders that for which implantable neurostimulation systems may be applied include tic disorders, such as Tourette's disorder; mood disorders, such as major depressive disorder and bipolar disorder; and anxiety disorders, such as obsessive-compulsive disorder. Typically, a neurostimulator will be programmed to deliver stimulation to a particular nerve or region of a patient's brain on either a continuous or scheduled basis (sometimes referred to as "open-loop" stimulation) or in response to signals from the patient that are detected by the neurostimulator (sometimes referred to as "closed-loop" stimulation and "responsive" stimulation).

One such closed-loop, responsive neurostimulation system for the treatment of epilepsy has been used to deliver electrical stimulation via electrodes implanted in the brain (deep brain electrodes) and/or on the surface of the brain (cortical electrodes) in response to what the system recognizes as a neurological event (e.g., a seizure, onset of a seizure, or a precursor to a seizure). This system is described, among other places, in U.S. Pat. No. 6,016,449, issued Jan. 18, 2000 to Fischell et al., entitled "System for the Treatment of Neurological Disorders." The disclosure of U.S. Pat. No. 6,016,449 is incorporated by reference herein in the entirety.

One or more signal processing techniques and/or algorithms typically are used in responsive systems to operate on signals being sensed by the neurostimulator from the patient in order to identify when a neurological event of interest has occurred or is occurring. Especially in cases where the neurostimulation system is wholly implantable, the robustness or accuracy or precision of these signal processing techniques usually is limited by design constraints such as limits on the amount of power the implantable device can consume before, for example, a battery has to be replaced or recharged. Typically, the signal processing techniques and associated algorithms include signal summing, squaring, subtracting, amplifying, and filtering.

Generally, the signal processing techniques and associated algorithms are used to test the signal(s) being sensed by the neurostimulator against a predetermined threshold or thresholds and, if a particular threshold is exceeded, the neurostimulator system will register the detection of an event or condition. In many neurostimulation systems, the detection of an event triggers delivery of a particular therapy (e.g., delivery of a stimulation pulse of certain amplitude, pulse width, frequency and waveform shape; delivery of a volume of a drug; or delivery some other stimulus, such as a sensory stimulus (auditory, visual, etc.); or some combination of stimuli.) Optimally, the thresholds identified will maximize the likelihood that the neurological event or condition of interest will be detected, and minimize the likelihood of "false positives," that is, conditions under which a threshold is exceeded but the event or condition of interest is not, in fact, occurring. U.S. Pat. No. 6,459,936, issued Oct. 1, 2002 to Fischell et al. for "Methods for Responsively Treating Neurological Disorders" describes some of these signal processing techniques and threshold-setting objectives. The disclosure of U.S. Pat. No. 6,459,936 is incorporated by reference herein in the entirety.

Some examples of particular signal processing techniques and/or algorithms include a half wave detector, a line length analysis, and an area function analysis, each of which is described at a high level herein and more fully in, for example, U.S. Pat. No. 6,473,639, issued Oct. 29, 2002 to Fischell et al., entitled "Neurological Event Detection Procedure Using Processed Display Channel Based Algorithms and Devices Incorporating These Procedures," U.S. Pat. No. 6,480,743, issued Nov. 12, 2002 to Kirkpatrick et al., entitled "System and Method for Adaptive Brain Stimulation," and U.S. Pat. No. 6,810,285, issued Oct. 26, 2004 to Pless et al. for "Seizure Sensing and Detection Using an Implantable Device." The disclosures of U.S. Pat. Nos. 6,473,639, 6,480,743, and 6,810,285 are each incorporated by reference herein in the entirety.

A half wave detector measures the occurrence of what are predefined to constitute half waves in an impinging electrocorticographic signal, or more generally, an electroencephalogic (EEG) signal from a patient within a specified half wave time window. (That is, in order to constitute or qualify as a "half wave" the impinging signal may have to have a certain amplitude or frequency, and the slope of the waveform may have to change to a predetermined degree.) The number of half waves occurring in one window is compared to a threshold value for a number of half waves. If the number of detected half waves exceeds the threshold, then detection of an event (e.g., onset of an epileptic seizure) is registered and certain therapy may be triggered (or at least further processing of signals from the patient might be accomplished in order to decide whether to deliver therapy). The half wave detector can be likened to a band pass filter insofar as it will identify an event or condition as detected based on such parameters as minimum and maximum frequencies and/or amplitudes.

A "line length" analysis can be undertaken by (1) accumulating the sample-to-sample amplitude variation in an EEG signal within a predefined time window (or normalizing the line lengths per unit time) (i.e., adding up all the line lengths that represent how much variation the signal in the samples is undergoing); (2) accumulating the sample-to-sample amplitude variation in the signal within the next window (of the same predefined, duration or normalized to the same time unit); and (3) comparing the total line lengths of the first window to the second window. If the sum of the line lengths in the subsequent window is 200% greater than the sum of the line lengths in the first window, then this might suggest that an event or condition of interest has been detected, since the signal measured in the second window would seem to be varying a lot more than the signal in the first window. The percent difference between the accumulated line lengths therefore can be used as a threshold parameter, because when the percent difference is increased, it will tend to decrease the sensitivity of detection and lower the detection rate, and when the percent difference is decreased, it will tend to increase the sensitivity of detection and thus increase the detection rate.

An "area function" analysis can be accomplished by calculating the area under the curve of a signal incident on a window having a predetermined length of time and then comparing it to the area under the curve for the same incident signal in a next window of time having the same predetermined duration. Alternatively, the samples used in calculating the area under the curve can be normalized per unit time, so that samples taken in different length windows can be meaningfully compared. An incident signal that is hovering around zero on the y axis will have a small total area as compared to an incident signal that is more active, e.g., one that is oscillating between the most positive and the most negative possible values on the y axis. Thus, if the change in area for a signal from one window to a subsequent window is large, this may suggest that the event or condition of interest is occurring. The area differences from window to window could be compared to a percent difference threshold, for example, a threshold of 250%, such that if the total area in a subsequent window is 250% greater than it was in a previous window, the threshold is met.

Ideally, the threshold above which an event or condition should be detected should be adjustable depending on variables such as the patient's physiological condition at different times. For example, where a closed-loop neurostimulation system is being used to treat epilepsy, the signals representative of the occurrence of seizures (or of the onset or precursors of seizures) may be quite different depending upon such things as the time of day, the time of the month, whether the patient is awake or sleeping, etc. It would be desirable to vary the value of a given threshold at those different times to optimize detection of the events of interest. As a practical matter though, most signal processing techniques that might be used to reset the threshold values based on time of day or changing physiological states of the individual patient would be complex and therefore would consume considerable computational power, which would make them less desirable, especially when the detection signal processing is implemented in an implantable device. The threshold values therefore are usually fixed relative to time of day or changing physiological conditions of a patient at least for the time between the patient's visits to the clinician. That is, the threshold values can be adjusted by the clinician during an office visit to either increase or decrease the sensitivity of the detector, but then they will remain fixed until the patient comes in for his or her next visit.

However, the ideal threshold for a given parameter used for detection may vary with a particular physiological condition, such as hormonal changes that might occur over a female patient's menstrual cycle. Further examples of when the optimal value for a given threshold might vary over time because the EEG signals measured at those time are quite different include between sleep and wake cycles, when medications are at different levels of concentration in a patient's system, and when a patient is sleep deprived or under unusual stress.

In addition, and where detection of an event or condition is associated with delivery of a therapy or treatment (e.g., electrical stimulation), the clinical efficacy of the detection/stimulation combination may depend on delivery of a minimum amount of stimulation to the central nervous system, just as the efficacy of some drug therapies depend on a minimum dose of the drug per day. Detection thresholds that are too low may result in a system that does not stimulate enough, or quickly enough, to alter the activity of the central nervous system in the desired manner (e.g., to control seizures).

Similarly, and again when detection is used to trigger electrical stimulation therapy, too sensitive a detector may result in more frequent stimulation than the central nervous system can accommodate, and the central nervous system therefore may not be as effectively modulated as when less frequent stimulation is delivered. In addition, a neurostimulator that detects and stimulates in response to the detections will have time constants associated with the feedback, sensing and stimulation subsystems. Thus, setting a detection threshold that is too low may result in a detection rate that exceeds the dynamic capabilities of the system. If this occurs, not all pathologic activity may be appropriately detected and stimulated or stimulation may be delivered too late to, for example, have the desired effect on epileptiform activity.

Further, asking the clinician to identify threshold values for parameters that will affect the detection rate can result in some frustration, as not all clinicians may have the depth of technical understanding about how the neurological event detector operates in order to choose optimum values. For example, for a responsive neurostimulator, a clinician likely would more appreciate a system that would allow him or her to specify a minimum "dose" of stimulation per day, which would correspond to a particular detection rate, and then have the system automatically choose the parameters to use as thresholds and to set the values for those parameters that will achieve that particular detection rate.

SUMMARY

Before the present systems, devices and methods are described, it is to be understood that this disclosure is not limited to the particular systems, devices and methods described, as these may vary. It is also to be understood that the terminology used in the description is for the purpose of describing the particular versions or embodiments only, and is not intended to limit the scope.

It must also be noted that as used herein and in the appended claims, the singular forms "a," "an," and "the" include plural references unless the context clearly dictates otherwise. Thus, for example, reference to a "threshold" is a reference to one or more thresholds and equivalents thereof known to those skilled in the art, and so forth. Unless defined otherwise, all technical and scientific terms used herein have the same meanings as commonly understood by one of ordinary skill in the art. Although any methods, materials, and devices similar or equivalent to those described herein can be used in the practice or testing of embodiments, the preferred methods, materials, and devices are now described. All publications mentioned herein are incorporated by reference. Nothing herein is to be construed as an admission that the embodiments described herein are not entitled to antedate such disclosure by virtue of prior invention.

Described here are systems, including devices and methods, for automatically adjusting the values of selected parameters which values are used as a threshold for determining whether an event or condition of interest has been detected in a patient. Detection of the event or condition may initiate delivery of a certain therapy or treatment to the patient, including but not limited to electrical stimulation, auditory or visual stimulation, or drug therapy. The parameters that are used to define the thresholds have a known effect on the rate at which the event or condition of interest will be detected. A target detection rate is established based upon a predicted or arbitrary number of occurrences of the event or condition, for example, 1000 occurrences of the event or condition per day.

An evaluation time interval is selected in which to compare the target defection rate to the actual number of events or conditions detected within that evaluation interval. If the target detection rate is different from the measured detection rate, the threshold values are adjusted upwardly or downwardly, as appropriate, following or during each evaluation interval, to minimize the difference. The target detection rate is normalized based on the particular evaluation interval or intervals selected. For example, if the target detection rate is 2400 events of interest per day, and the evaluation interval is one hour, then the normalized target detection rate would be 100 events per hour.

In an embodiment, a method for approximating a target detection rate for a neurological event with a neurological event detector intended for use with a human patient may include identifying a target detection rate for the neurological event, monitoring electrographic signals incident on the neurological event detector, comparing each electrographic signal to a threshold value for a parameter the variation of which has a predictable effect on a detection rate of the neurological event, measuring a rate at which the electrographic signals exceed the threshold value to determine a measured detection rate, comparing the measured detection rate to the target detection rate, and adjusting the threshold value to minimize a difference between the measured detection rate and the target detection rate.

In an embodiment, in a neurological event detector intended for use with a human patient, a method for minimizing the difference between a target detection rate and a measured detection rate for a neurological event may include identifying a target detection rate for the neurological event, monitoring electrographic signals sensed from the human patient by the neurological event detector, comparing each electrographic signal to a threshold value for a parameter the variation of which has a known relationship to a sensitivity of the neurological event detector to register a detection of the neurological event, measuring a rate at which the electrographic signals exceed the threshold value to determine a measured detection rate, comparing the measured detection rate to the target detection rate, and adjusting the threshold value to minimize a difference between the measured detection rate and the target detection rate.

In an embodiment, a neurological event detector intended for use with a human patient to detect a neurological event may include at least one sensor for receiving electrographic signals from the human patient, a detector for analyzing the electrographic signals to identify an occurrence of the neurological event whenever a threshold value for a parameter is exceeded, a memory in which a target detection rate is storable and from which the target detection rate is accessible, a comparator for comparing the measured detection rate to the target detection rate, and a parameter adjuster for adjusting the threshold value to minimize a difference between the measured detection rate and the target detection rate. Variation of the parameter may have a predictable effect on a defection rate of the neurological event, wherein an output of the detector is a measured detection rate.

BRIEF DESCRIPTION OF THE DRAWINGS

Aspects, features, benefits and advantages of the embodiments described herein will be apparent with regard to the following description, appended claims and accompanying drawings where:

DETAILED DESCRIPTION

Described here are systems, including devices and methods for automatically adjusting the threshold values for parameters used in detecting the occurrence of an event or condition of interest in a human patient, based upon the difference between a preselected target detection rate and an actual detection rate over one or more evaluation intervals. The systems, devices and methods primarily are described in the context of an implantable neurostimulator that is capable of detecting signals from a patient's brain that are believed to be indicative of the occurrence or onset of an epileptic seizure, or a precursor of an epileptic seizure, and then delivering stimulation to the patient's brain whenever a defection occurs. However, it will be apparent to one with skill in the art that the systems, devices and methods may be used with any feedback control system in which the change in a sensed parameter can be used identify the occurrence of an event or condition, so as to enable some type of response to detection of the event or condition. For example, in addition to or instead of delivering a responsive therapy, the response may include storing information corresponding to the detection or communicating information concerning the detection to another system or systems.

The description herein may also use the term "EEG" interchangeably with "ECOG" to refer to signals detected from the brain, whether the signals are detected from a cortical surface of the brain or from deep brain electrodes or otherwise, even though "EEG" is generally considered to be a broader term than "ECOG."

Figure 1:
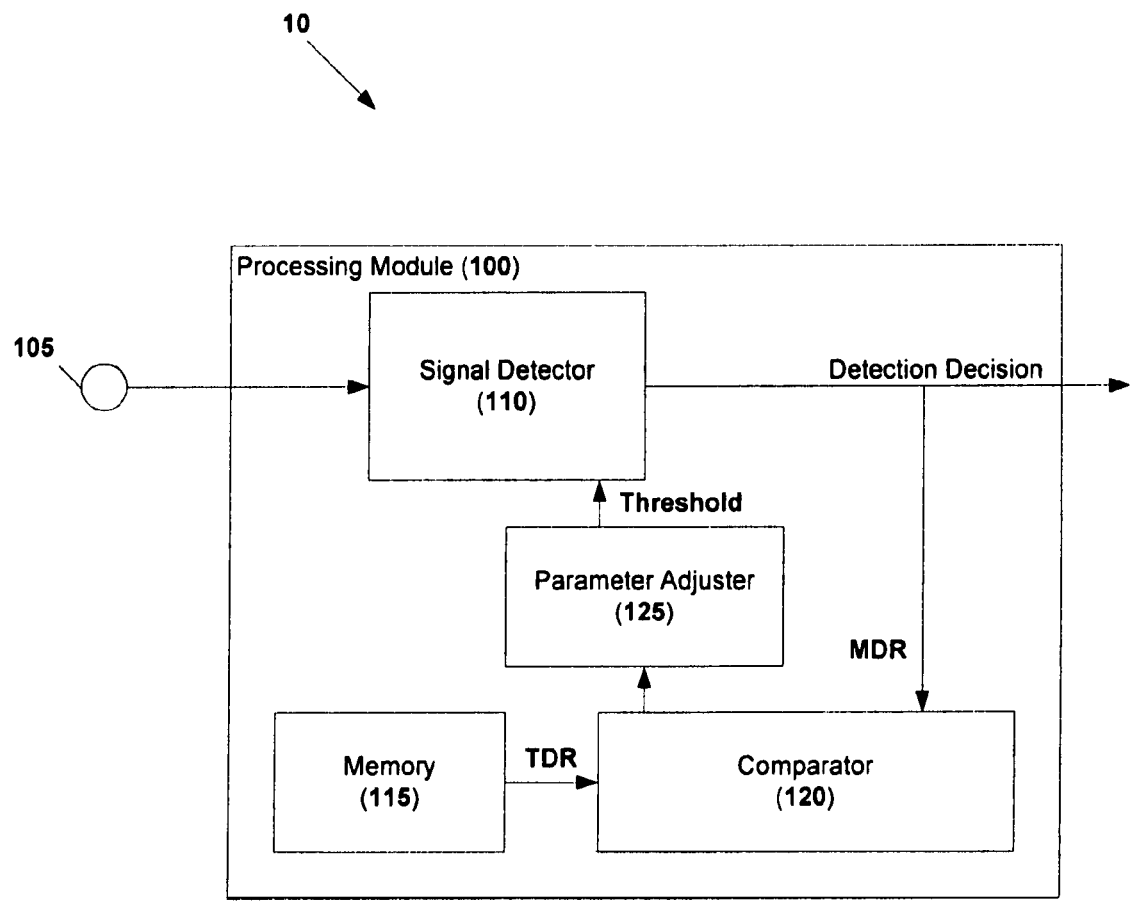
FIG. 1 depicts an exemplary block diagram for a neurological event detector according to an embodiment of the present invention.

FIG. 1 depicts an exemplary block diagram for a neurological event detector according to one embodiment. As shown in FIG. 1, the neurological event detector 10 comprises a processing module 100 that includes at least one sensor 105, a signal detector 110, a memory 115, a comparator 120 and a parameter adjuster 125. The at least one sensor 105 receives EEG signals from the patient and passes the EEG signals to the signal detector 110.

The signal detector 110 is configured to analyze the EEG signals to identify an occurrence of a neurological event when a threshold value for at least one parameter is exceeded. (A neurological event can be defined as occurring when just one threshold value is exceeded for one parameter, or as occurring when two or more thresholds for two or more different parameters are exceeded at about the same time.) Each parameter, when varied, has a predictable effect on a detection rate of the neurological event. More particularly, varying the value of a parameter will tend to increase or decrease the rate at which an event or condition of interest will be detected. Stated another way, varying the value of the parameter will tend to increase or decrease the sensitivity of the detector.

Examples of parameters include but are not limited to the following: difference between the accumulated line length from one signal sample to the next, the difference between the area under the curve from one signal sample to the next, and the number of half waves detected in a given signal sample. These parameters are discussed in more detail below in the context of the neurological event detector system, device and method.

In an embodiment, one parameter for which a threshold value is set may represent a difference between the accumulated line lengths for a first EEG signal measured in a predetermined window of time and the accumulated line lengths for a subsequent EEG signal measured in a window of time of the same duration. This parameter of accumulated line length is a general indication of the activity level of the EEG in the time window. If the signal is relatively inactive when first measured in the first window and then becomes relatively active when next measured in the second window, the difference between the accumulated line lengths in the first window and the accumulated line lengths in the second window will be greater than the difference would be in the EEG remained relatively inactive as between the first and the second measurements. When the difference in accumulated line lengths is sufficiently large, the difference may be used as one threshold for identifying that, e.g., an EEG signal constituting a precursor to a seizure, has occurred.

In an alternate embodiment, the accumulated line lengths for EEG signals may be measured in windows of time having different durations. In such an embodiment, the accumulated line lengths may be normalized to, for example, a unit duration. The difference between the normalized accumulated line lengths may then be determined.

Determining which values for the percent difference are appropriate for a particular patient may be somewhat of a trial and error process. However, for patients for whom some baseline EEG information has been recorded, a clinician can look for the events of interest and judge how much the signal seems to be changing, on average, at the clinical onset of a seizure, for example. For one patient, the clinician might estimate that the activity level of the signal at the onset of an electrographic seizure tends to change by about 300%. In this case, an initial value for the threshold parameter percent difference in accumulated line lengths could be 300%, such that if the difference in line lengths from one window to the next reaches or exceeds 300%, then the detector will register detection of an event. The degree to which the EEG activity changes for the same patient at seizure onset, however, may be different depending on, for example, whether the patient is awake or sleep (e.g., the change in activity may be less when the patient is sleeping than when he is awake). Thus, when the patient is sleeping, a more appropriate value for the threshold parameter of the percent difference in accumulated line lengths might be 75%.

Figure 2:
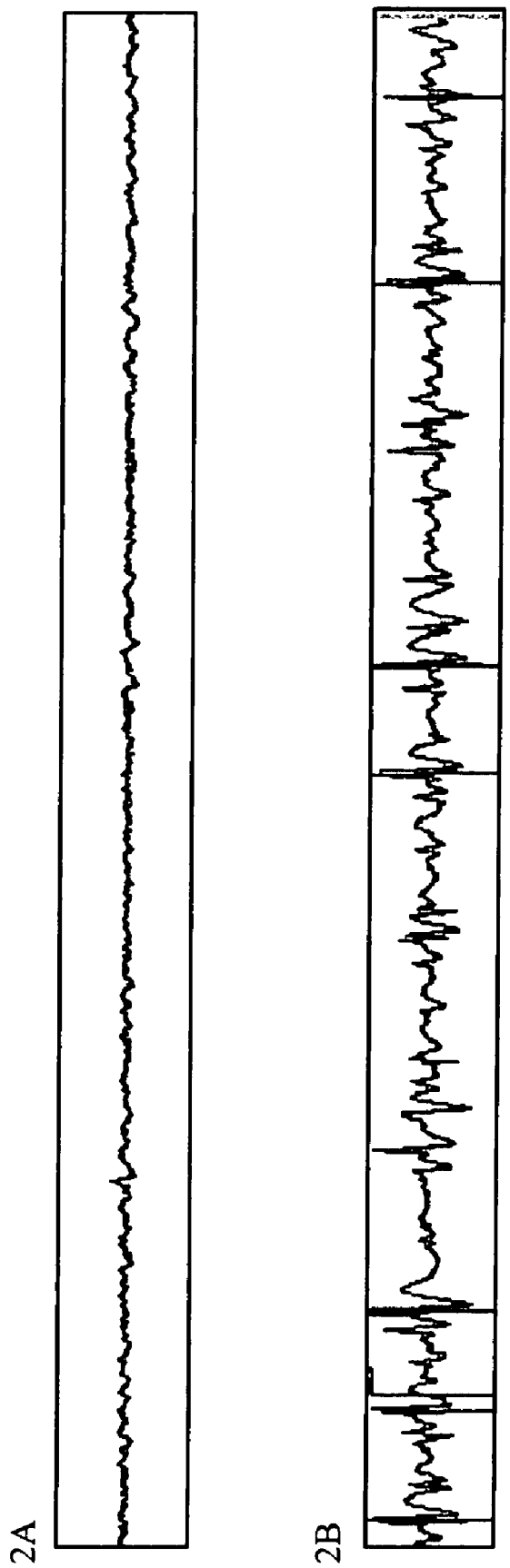
FIG. 2A depicts an exemplary electrocorticogram signal during a period of low brain activity.
FIG. 2B depicts an exemplary electrocorticogram signal during a period of high brain activity.

Referring now to FIG. 2, FIG. 2A shows an EEG of relatively low activity and FIG. 2B shows an EEG of relatively high activity. Thus, the difference in accumulated line lengths that needs to be met or exceeded to identify detection of an event may be less when the EEG is relatively inactive than it is when the EEG is relatively active. That is, the most appropriate threshold for an active EEG may be 300% but the most appropriate threshold for a relatively inactive EEG for the same patient may be only 75%.

When the threshold value is fixed at 300%, signals that should be identified as events when the patient's EEG is relatively inactive may not be so identified. In contrast, if the threshold value is fixed at 75%, too many signals may be identified as detected events.

The threshold or threshold values associated with the signal detector 110 will determine the actual or measured detection rate (MDR) over a given evaluation time window. More particularly, if a threshold is set so that an event will be detected whenever the threshold value for the parameter meets or exceeds "100," and the evaluation window is one hour, then the number of signals that occur in one hour for which the threshold of "100" is met or exceeded will be the measured detection rate. If the threshold value is met or exceeded ten times in one hour, then the MDR will be 10 per hour.

The memory 115 is used, among other things, for storing and providing access to a target detection rate (TDR). A clinician may set the TDR or adjust a previously set TDR during an office visit with the patient. For a given patient, a target detection rate can be selected based on criteria such as a predicted rate of events per day or even an arbitrarily selected rate of events per day that later can be adjusted after data on the patient's actual rate of occurrence for the event has been obtained. The more baseline EEG data the clinician has for a given patient, the more precisely he or she is likely to be able to select an appropriate TDR.

If the event of interest is the occurrence of an EEG signal that is believed to have characteristics that indicate that the onset of a seizure is imminent, then the target detection rate may have a range of 1 to 10,000 per day, with typical values for particular patients being in the range of 100-1000 per day. Similarly, if the neurological event detector is also being used to trigger a therapy regimen whenever events are detected, the target detection rate can be based on the clinician's assessment of how much therapy should be delivered to the patient per day (e.g., a minimum of a thousand stimulations per 24-hour period).

The comparator 120 is configured to receive the TDR from the memory 115 and compare the TDR to the MDR. The comparator 120 provides the result of the comparison to the parameter adjuster 125.

The parameter adjuster 125 is configured to adjust the threshold value in order to minimize a difference between the MDR and the TDR. More particularly, if the comparator 120 determines that the MDR is greater than the TDR, the parameter adjuster 125 may increase or decrease (as appropriate) the threshold value for the parameter, which increase or decrease in turn will change the actual rate of detection, so that the MDR measured over the evaluation interval will come closer and closer to the TDR and eventually the difference between the MDR and the TDR will approximate zero.

For example, if the MDR is greater than the TDR, it means that the system is registering more signals as "events" than predicted or expected according to the TDR. In this situation, the intent is to adjust the parameter to reduce the number of signals that are being identified as "events" so as to bring the MDR closer to the TDR. If one parameter for which a threshold value is set is the difference in accumulated line lengths in consecutive measurement windows, then increasing the value of the threshold will correspond to decreasing the number of signals that are identified as events—the greater the difference, the fewer the number of signals that will qualify as "events." Therefore, increasing the threshold value for this parameter should bring the MDR closer to the TDR.

On the contrary, if the MDR is less than the TDR, this means that the system is registering fewer signals as "events" than predicted or expected, and decreasing the difference required in accumulated line lengths from window to window should translate to more signals being identified as events (e.g., because less of a change in the activity level of the impinging signal is required before an event, is identified as having been detected), and the MDR should rise towards the TDR.

The degree to which the value of any given parameter can be automatically adjusted by the system preferably is bounded by minimum and maximum threshold values, and a fixed range of step sizes corresponding to how much a parameter value can be adjusted upwardly or downwardly after a given comparison of MDR to TDR. More specifically, if the range of possible threshold values for the accumulated line length difference parameter is 75% to 300%, 75% may be established as the minimum threshold value and 300% as the maximum threshold value. If it is considered desirable to limit the increase or decrease in that parameter to 25% whenever the threshold value is adjusted, the step size would be set at 25%. A range of possible step sizes can be available from which the physician can choose.

The neurological event detector 10 thus enables varying the threshold value(s) that are used to register detection of an event or condition at various times based on an expected or predicted number of events for a predetermined period, such as a day, week or month. As the clinician's experience with a particular patient grows, any or all of the TDR, the evaluation interval, the minimum, and maximum threshold values, and the step size can be adjusted or fine tuned for the patient to try mid maximize the detection of the event or condition of interest, e.g., the number of signals that are believed to be precursors to seizure.

Another example of a parameter for which threshold values can be set to prompt detection of an event, or condition is an area difference parameter. The area difference parameter is similar to the accumulated line length difference parameter previously described, insofar as it involves comparing the accumulated area under the curve of a first sample of the impinging EEG signal to the accumulated area under the curve of a subsequent or second sample. When the difference in areas between the two samples is great, it generally can be interred that the activity level of the signal from one sample to the other is changing a lot. When the difference in areas between the two samples is small, the opposite can generally be inferred, that is, that the activity level of the signal from sample to sample is not changing much at all. Thus, if a threshold value for this parameter is set too low, it may identify more signals as "events" than actually should be registered as detected events. On the other hand, if a threshold value for this parameter is set too high, it may register fewer detected events than it should. Moreover, the optimal value for this parameter may be different depending upon the time of clay or the patient's physiological condition. For example, if the patient's physiological condition results in an EEG that is relatively inactive over a selected evaluation interval, such as an hour, then the degree of difference in area from one signal sample to another which ought to correspond to detection of an event might be less than when the patient's physiological condition results in a relatively active EEG.

In this situation, a TDR might be set at 240 events per day, where the event might be a signal corresponding to what is believed to be a precursor to a seizure. The threshold value of the area difference parameter might be set at 50%, such that when the area under the curve in a subsequent sample differs from the area under the curve for a previous sample by 50% or more, an event is detected. If the evaluation interval is selected as one hour, then the normalized TDR would be 10 precursor signals per hour. If the patient's EEG is relatively inactive over an hour, then the MDR may be less than the TDR because the EEG signal is not changing significantly enough from measurement window to measurement window in order to exceed the 50% threshold for the area difference parameter, but the patient nevertheless be experiencing signals that are thought to be precursors of seizures. Accordingly, the threshold value of the area difference parameter may be decreased by a step of 10%, to see whether more events will be detected with the lower threshold. If when the MDR and TDR are next compared, the difference between them is still much greater than zero, the threshold value can be downwardly adjusted by 10% again, so that now the threshold is 30%, and hopefully more samples in the relatively inactive signal will now be identified as detected events. This adjustment process may continue until a minimum value for the area difference threshold is reached, such as 20%. The minimum and maximum values for the threshold, as well as the step size for the increments or decrements of that value, can be adjusted by the clinician as appropriate.

Still another example of a parameter for which threshold values can be set to prompt detection of an event or condition is the number of half-waves occurring in a signal over a pre-selected period of time, which number is derived from a signal processing technique that can be likened to a band-pass filter.

Each of the signal processing techniques which result in calculation and comparison of line lengths, areas under the curve, and half-wave detection are described more fully in, for example, U.S. Pat. No. 6,810,285.

As noted above, threshold values for more than one parameter can be used in combination to determine whether detection of an event should be deemed to have occurred. For example, if for a given signal sample, the half-wave detector threshold value is met or exceeded but the area difference is not met or exceeded, then an event nonetheless may be identified as having occurred. Alternatively, both the area difference threshold and the accumulated line length threshold may have to be met or exceeded, regardless of whether the number of half waves has been met exceeded, before an event is registered as detected.

While all possible parameters have not be discussed in detail here, it will be apparent that threshold values for any parameter that has a known and/or predictable effect on the rate of detection of an event or condition of interest can be used to good effect with the neurological event detector system described herein. Moreover, as the technology for designing and implementing implantable medical devices continuous to improve and advance, it is envisioned that more and more sophisticated signal processing techniques can be used with the implantable medical devices, without exceeding computational, power or other design constraints. This increase in sophistication likely will lead to more and more parameters the threshold values of which can be used to automatically adjust the rate of detection of events or conditions of interest.

The disclosed invention provides an elegant and uncomplicated way of adjusting the threshold above (or below) which an event or condition is identified as having been detected without consuming excessive power or requiring excessive interaction between clinician and patient.

In an embodiment, the detection threshold is dynamically and automatically adjusted based on the activity level of the detected signal. For example, during a period of relatively low activity, such as is depicted in FIG. 2A, the detection threshold is caused to decrease over time. Likewise, during a period of relatively high activity, such as is depicted in FIG. 2B, the detection threshold is caused to increase over time. Automatic adjustment of the detection threshold results in a more even distribution of neurostimulation therapy over a broader dynamic range of background EEG activity.

Figure 3:
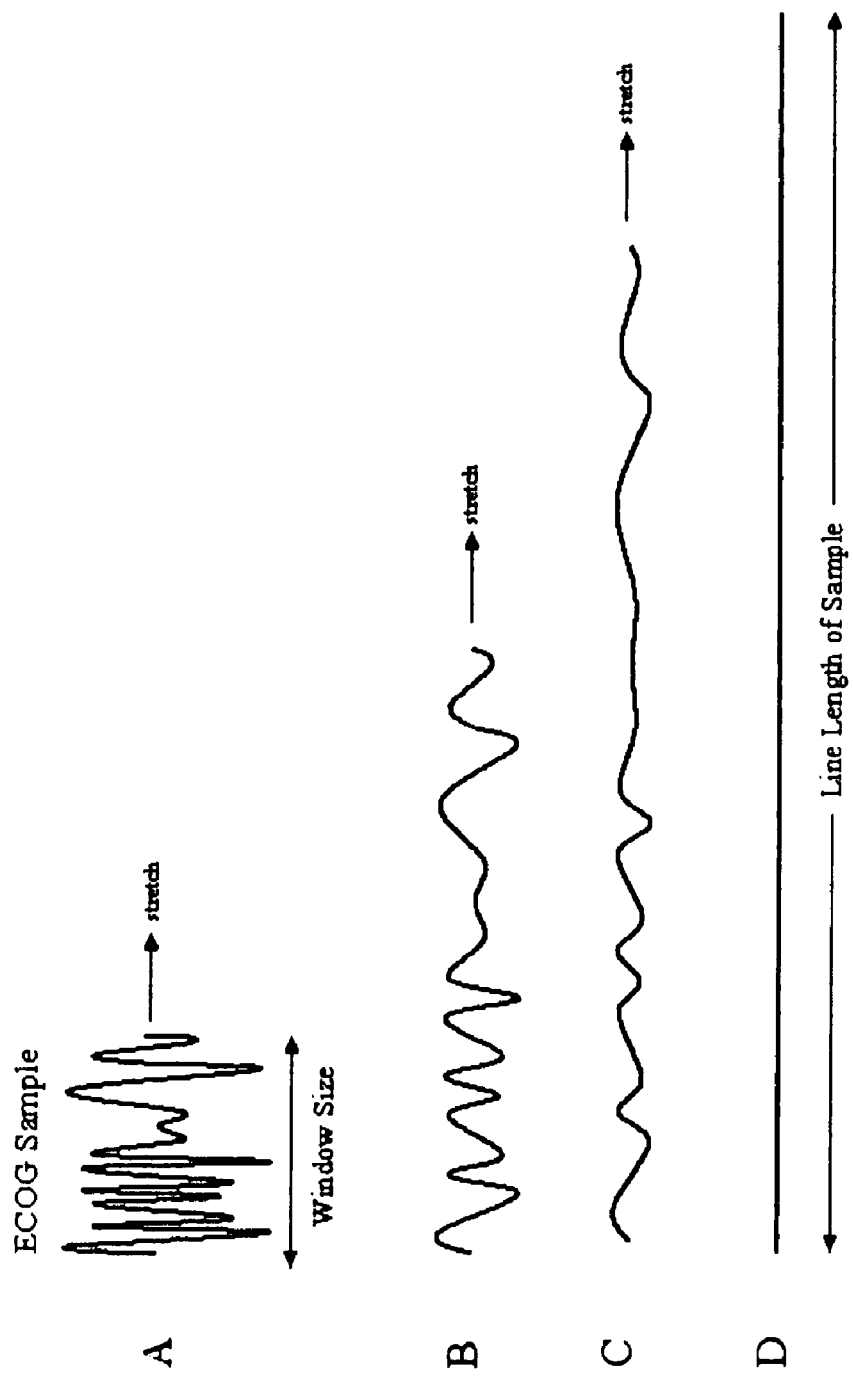
FIGS. 3A-D depict an exemplary ECOG signal and a graphical representation of a line length determination according to an embodiment of the present invention.

Line length detection for an EEG signal can be conceptualized by considering the EEG signal to be a piece of string that can be stretched until straight, as represented in FIGS. 3A-D. In FIG. 3A, a portion of an ECOG signal within a window having a known duration is shown. As shown in FIGS. 3B and 3C, the ECOG signal is stretched until it is completely linear (as shown in FIG. 3D). The signal of interest is then the length of FIG. 3D divided by the window size for FIG. 3A. This results in a line length, per time value (the "Normalized Line Length" or "NLL"). By normalizing the line lengths, comparisons can be made between signals collected within windows having different time periods. Although FIGS. 3A-D pertain to an ECOG signal, any EEG signal may be used within the scope of this disclosure.

Figure 4:
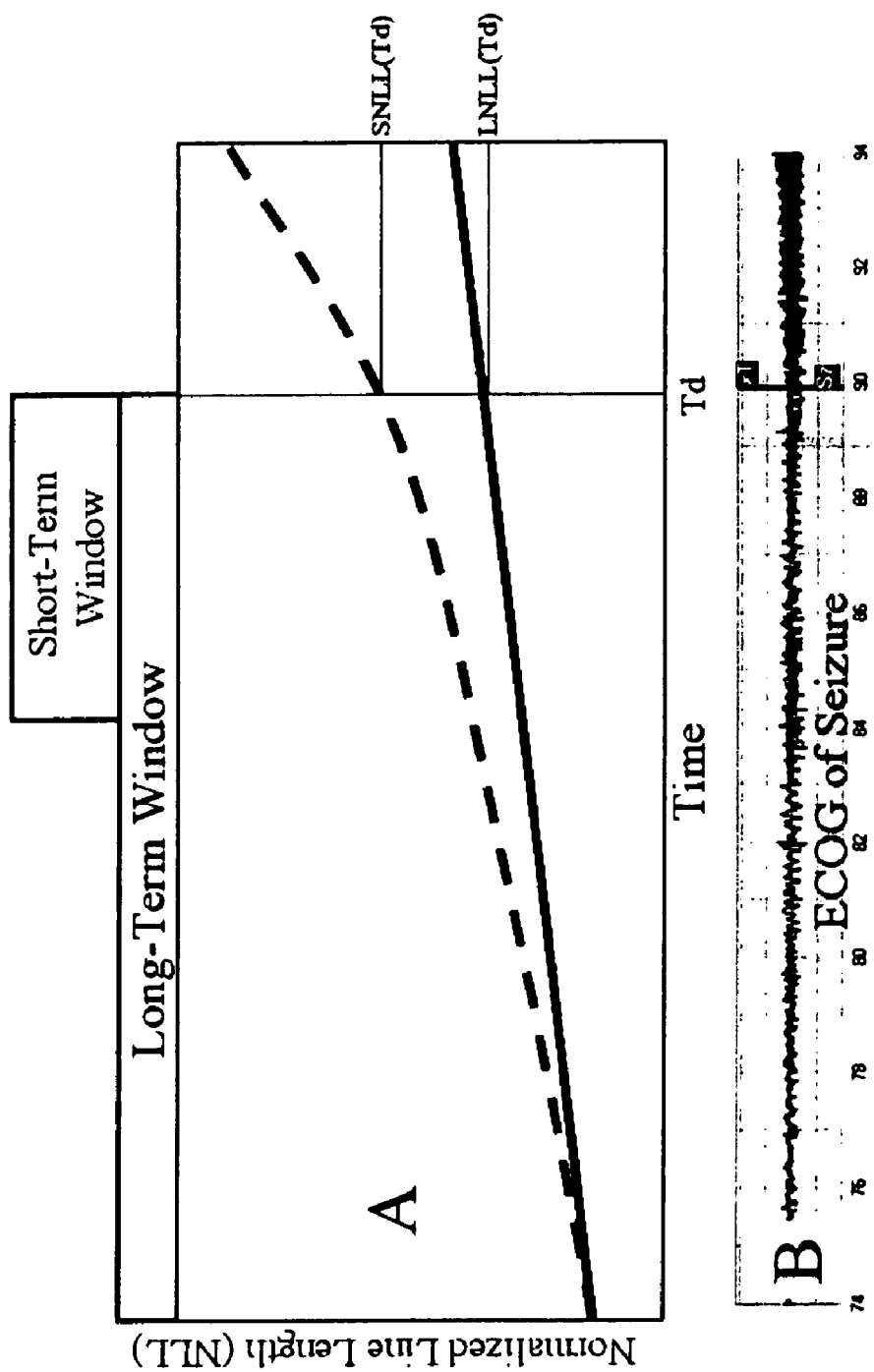
FIGS. 4A and 4B depict a method for detecting a neurological event based on a line length measurement according to an embodiment of the present invention.

To defect a neurological event within the line length signal, comparisons are made over time to look for changes in the NLL. FIGS. 4A and 4B depict a method for detecting a neurological event based on a line length measurement according to an embodiment of the present invention. FIG. 4B depicts an epileptic seizure recorded from intracranial sensors. As the seizure evolves, the NLL increases. To detect the signal, a comparison is made on a periodic basis between NLL values collected using different-sized time windows. In FIG. 4A, a short-term window (e.g., having a span of hundreds of milliseconds to several seconds) and a long-term window (e.g., having a span of several seconds to hours) are shown. The NLL for the short-term window is referred to as the Short-Term NLL or SNLL and the NLL for the long-term window is referred to as the Long-Term NLL or LNLL. As shown in FIG. 4A, the SNLL and LNLL increase as the seizure evolves. However, the LNLL does not increase as rapidly as the SNLL because it averages in additional data (e.g., data from when the ECOG signal was less active and had lower line length signal content). The variation in the rate of change between the SNLL and the LNLL permits detection of the seizure event. For example, the detection threshold may detect a neurological event when the SNLL exceeds the LNLL by 50%. This occurs in FIG. 4A approximately at time $T_d$.

The line length detector described above includes three parameters that could be used to control detection: the long-term window size (LTW), the short-term window size (STW) and the percent difference required for detection (PD). Of these parameters, only the PD is amenable to automatic control because the impact that an alteration in PD would have on the overall detection rate is known. That is, as the PD is increased, fewer ECOG (or EEG) signals will exceed the threshold and the MDR will decrease. Conversely, as the PD is decreased, more ECOG (or EEG) signals will exceed the threshold and the MDR will increase. Because of this predictability, automatic control of PD can enable a stable feedback mechanism. In contrast, automatic control of the STW or the LTW will not lead to a known effect because the result of adjusting the STW or the LTW will be dependent on the history, duration and amplitude of the signal.

Figure 5:
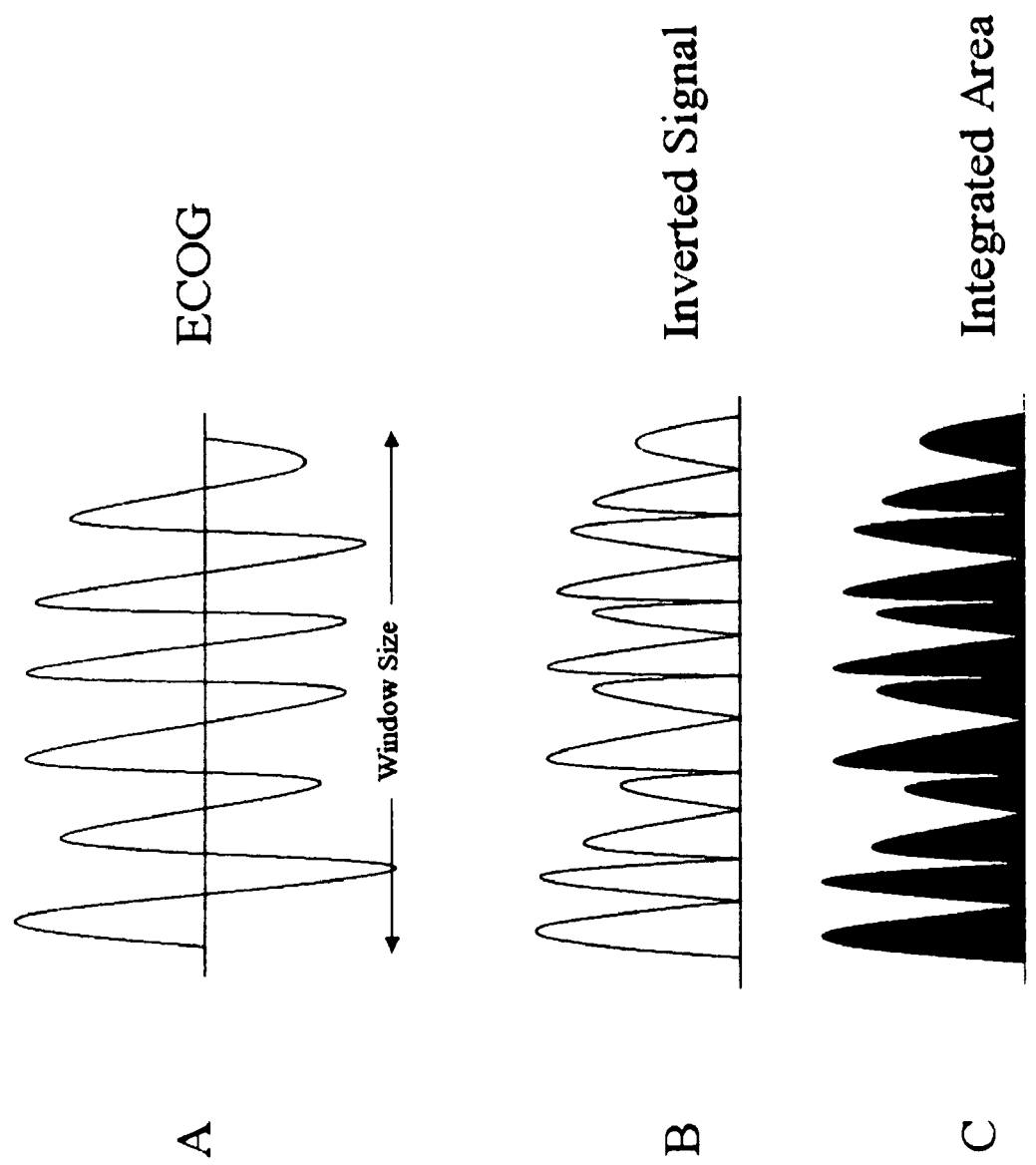
FIGS. 5A-C depict an exemplary ECOG signal and a graphical representation of an area determination according to an embodiment of the present invention.

Another method of detecting a neurological event is comparing the difference in area under the curve of incident EEG signals. Area difference analysis for an EEG signal can be conceptualized as represented in FIGS. 5A-C. In FIG. 5A, a portion of an ECOG signal within a window having a known duration is shown. FIG. 5B depicts a curve representing the absolute value of the ECOG signal of FIG. 5A (i.e., a rectified signal). FIG. 5C represents the area under the rectified signal of FIG. 5B as determined via integration over the window of known duration. A normalized area (NA) used for detection can be normalized by dividing the integrated area of FIG. 5C by the duration of the time window. By normalizing areas, comparisons may be made between signals collected within windows having different durations. Although FIGS. 5A-D pertain to an ECOG signal, any EEG signal may be used within the scope of this disclosure.

Figure 6:
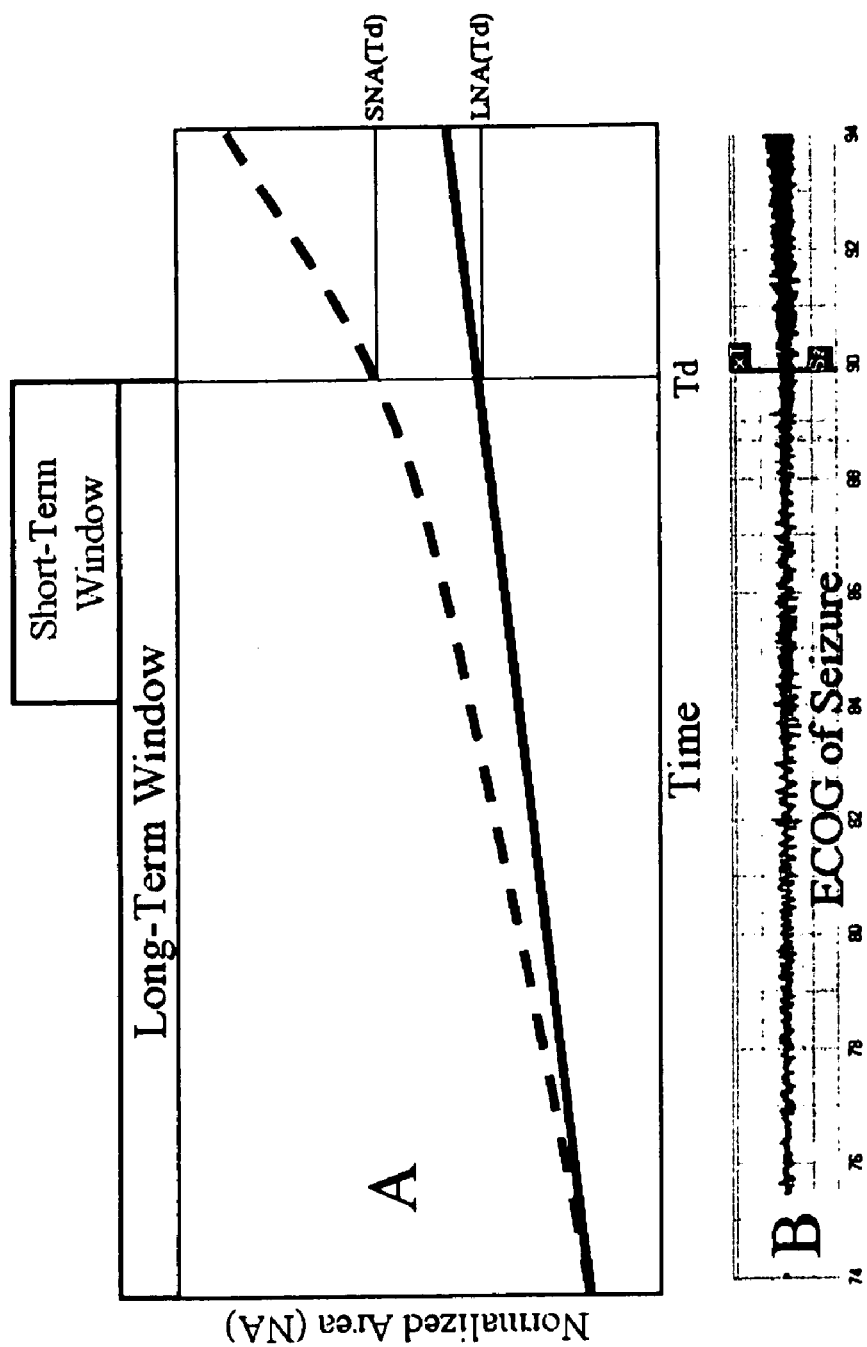
FIGS. 6A-B depict a method for detecting a neurological event based on an area measurement according to an embodiment of the present invention.

To detect a neurological event using the area difference analysis, comparisons of EEG signals incident on the neurological event detector are made over time to look for changes in the NA. FIGS. 6A and 6B depict a method for detecting a neurological event based on an area measurement according to an embodiment of the present invention. FIG. 6B depicts an epileptic seizure recorded from intracranial sensors. As the seizure evolves, the NA increases. To detect the signal a comparison is made on a periodic basis between NA values collected using different-sized time windows. In FIG. 6A, a short-term window (e.g., having a span of hundreds of milliseconds to several seconds) and a long-term window (e.g., having a span of several seconds to hours) are shown. The NLL for the short-term window is referred to as the Short-Term NA or SNA and the NA for the long-term window is referred to as the Long-Term NA or LNA. As shown in FIG. 6A, the SNA and LNA increase as the seizure evolves. However, the LNA does not increase as rapidly as the SNA because it averages in additional data (e.g., data from when the ECOG signal was less active and had lower area signal content). The variation in the rate of change between the SNA and the LNA permits detection of the seizure event. For example, the detection threshold may detect a neurological event when the SNA exceeds the LNA by 50%. This occurs in FIG. 6A approximately at time $T_d$.

The area difference analysis described above includes three parameters that could be used to control detection: the long-term window size (LTW), the short-term window size (STW) and the percent difference required for detection (PD). Of these parameters, only the PD is amenable to automatic control because the impact that an alteration in PD would have on the overall detection rate is known. That is, as the PD is increased, fewer ECOG (or EEG) signals will exceed the threshold and the MDR will decrease. Conversely, as the PD is decreased, more ECOG (or EEG) signals will exceed the threshold and the MDR will increase. Because of this predictability, automatic control of PD can enable a stable feedback mechanism. In contrast, automatic control of the STW or the LTW will not lead to a known effect because the result of adjusting the STW or the LTW will be dependent on the history, duration and amplitude of the signal.

Figure 7:
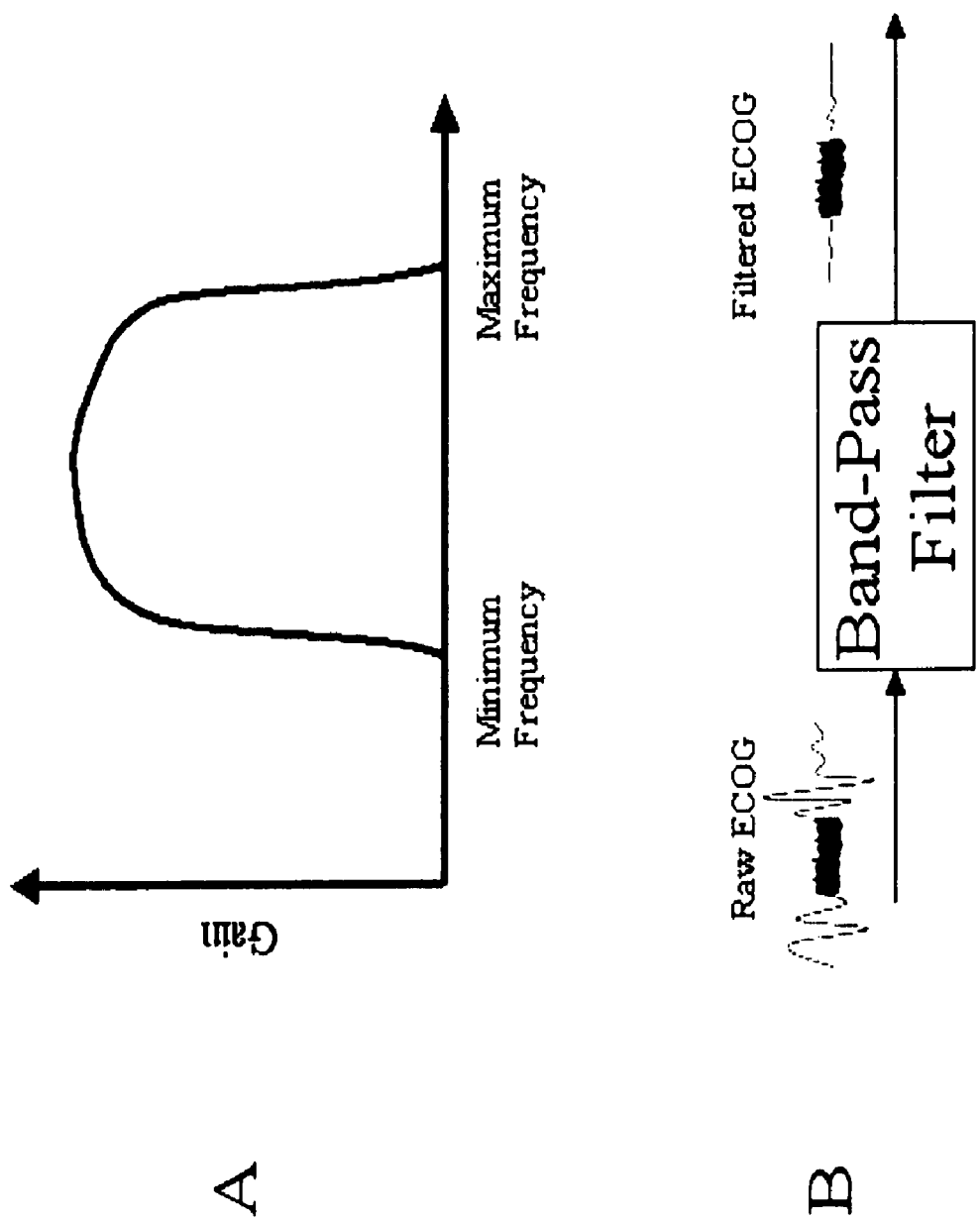
FIG. 7A depicts an exemplary frequency range for a band pass filter according to an embodiment of the present invention.
FIG. 7B depicts an operation of an exemplary band pass filter according to an embodiment of the present invention.

Still another method of detecting a neurological event is through use of a band-pass filter. Band pass detection for an EEG signal can be conceptualized as represented in FIGS. 7A-B. A received EEG signal is initially filtered by identifying minimum and maximum frequencies that will pass through the filter as shown in FIG. 7A. Adjustment of these parameters enables the detection process to ignore signal components outside of the frequency band between the minimum and maximum frequencies. The impact that the filtering process has on a raw EEG signal incident on the neurological event detector is shown in FIG. 7B. Although FIG. 7B pertains to an ECOG signal, any EEG signal may be used within the scope of this disclosure.

Figure 8:
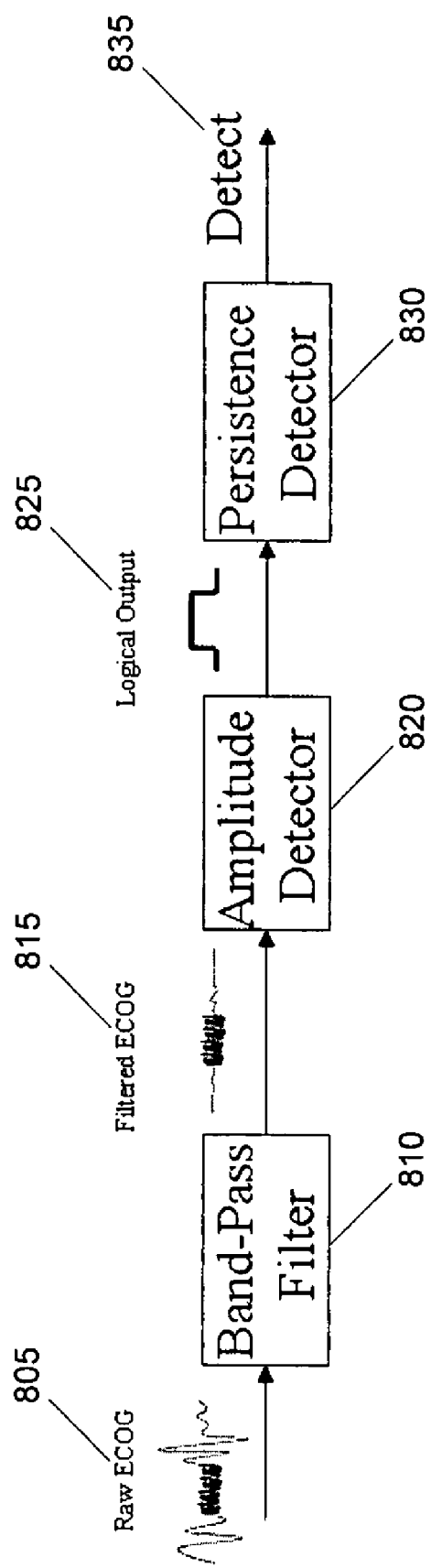
FIG. 8 depicts an exemplary system for detecting a neurological event according to an embodiment of the present invention.

Additional detection parameters for the band-pass filter would include the amplitude and the persistence, the use of which is depicted in FIG. 8. As shown in FIG. 8, the raw ECOG signal 805 passes through the band-pass filter 810 resulting in a filtered ECOG signal 815. An amplitude detector 820 is used to determine whether the filtered ECOG signal 815 exceeds an amplitude threshold. If so, a logical output 825 may be assigned a first value, such as a 'high' value. If not, the logical output 825 may be assigned a second value, such as a 'low' value. A persistence detector 830 is used to determine whether the logical output 825 has the first value for at least an amount of time determined by a persistence threshold. If so, an event is detected 835.

For the band-pass filter method described above, four parameters may control detection: the minimum frequency, the maximum frequency, the amplitude threshold and the persistence threshold. The amplitude threshold and the persistence threshold may be the most amenable to automatic control because the impact that an alteration in these parameters would have on the overall detection rate is known. That is, as the amplitude threshold is increased, fewer EEG signals will exceed the threshold and the MDR will decrease. Conversely, as the amplitude threshold is decreased, more EEG signals will exceed the threshold mid the MDR will increase. Similarly, as the persistence threshold is increased, fewer EEG signals will last sufficiently long to surpass the persistence threshold and the detection rate will decrease. Conversely, as the persistence threshold is decreased, more EEG signals will last sufficiently long to surpass the persistence threshold and the detection rate will increase. Because of this predictability, automatic control of the amplitude threshold and/or the persistence threshold can enable a stable feedback mechanism. Automatic control of the minimum and/or maximum frequencies may also be used because a wider bandwidth would allow more signals to pass that would exceed the amplitude and persistence thresholds. However, detection may be tuned to specific signals based on frequency content which could be negatively impacted by the automatic adjustment of the filter frequencies. Regardless of the parameter that is adjusted, system stability may depend upon automatically adjusting only a single parameter at a time to avoid a destabilizing interaction between parameters.

Figure 9:
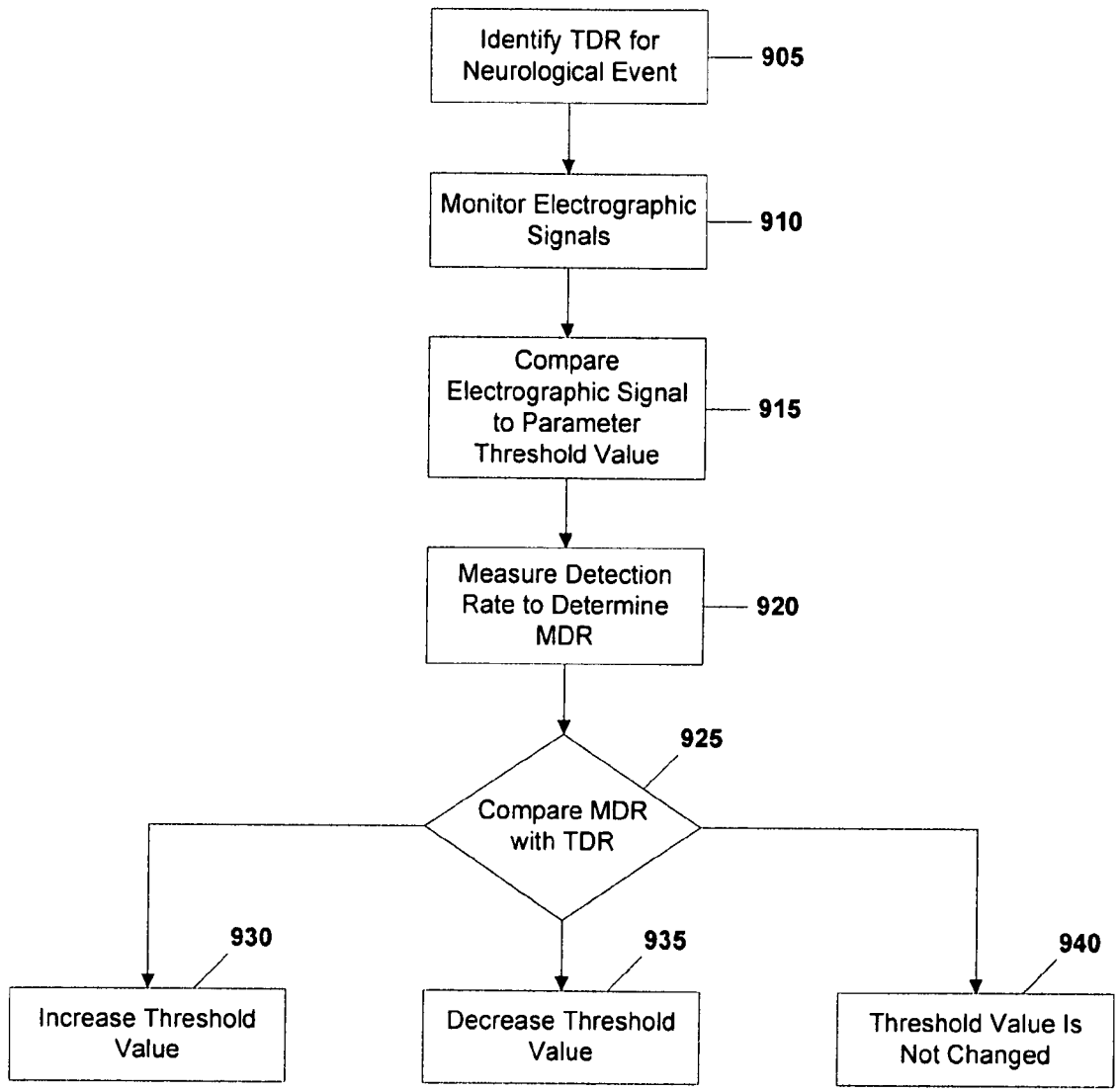
FIG. 9 depicts a flow diagram for an exemplary method of approximating a target detection rate for a neurological event with a neurological event detector according to an embodiment of the present invention.
Figure 10:
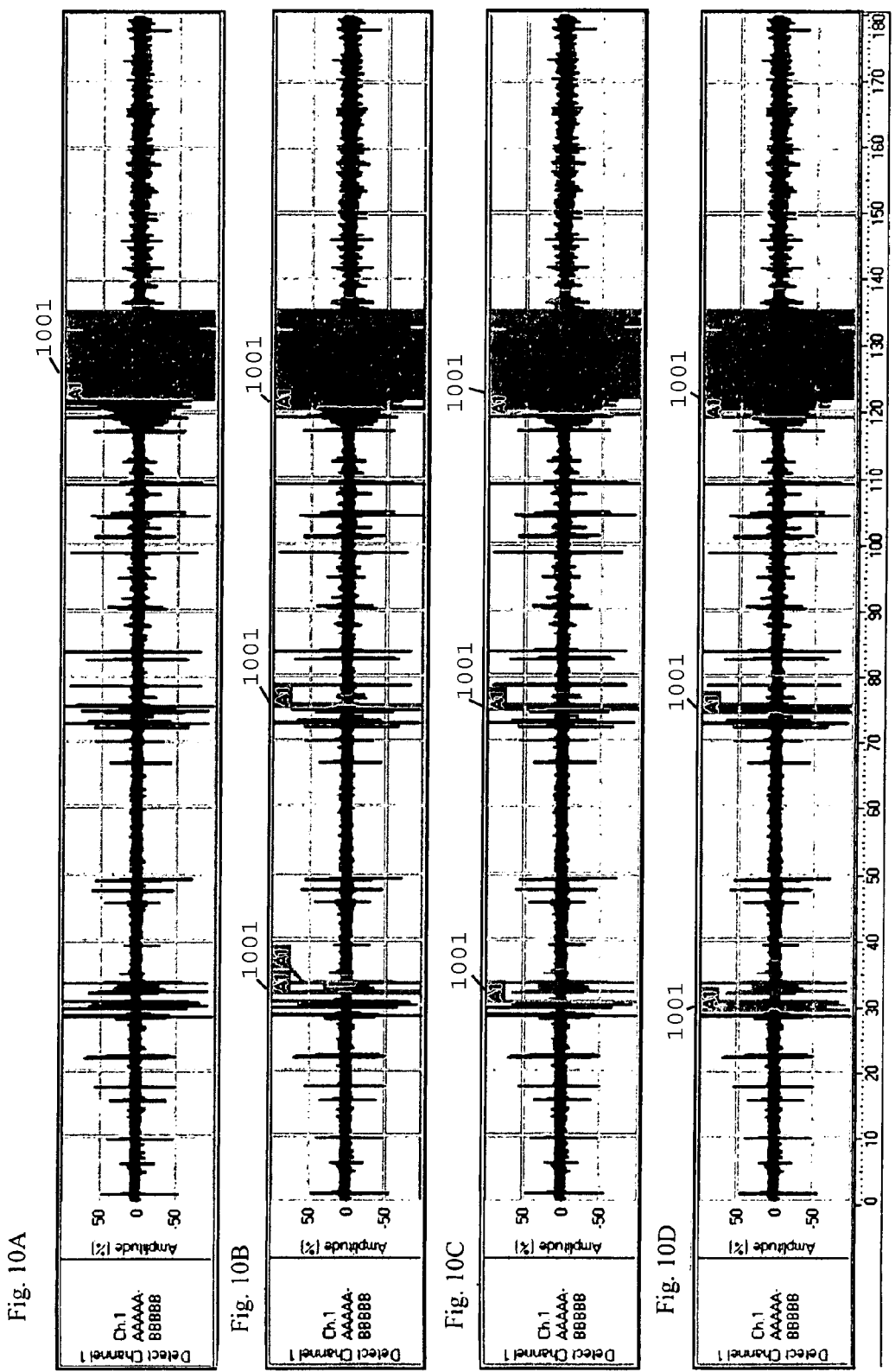
FIGS. 10A-D depict exemplary graphs of ECOG activity and detection for particular detection thresholds according to an embodiment of the present invention.

FIG. 9 depicts a flow diagram for an exemplary method of approximating a target detection rate for a neurological event with a neurological event detector according to an embodiment of the present invention. As shown in FIG. 9, a target detection rate for the neurological event may be identified 905. In an embodiment, the TDR may be identified 905 by retrieving a value for the TDR from a memory integral to or in communication with the neurological event detector. Electrographic signals incident on the neurological event detector may be monitored 910. For example, a sensor may provide the electrographic signals to a signal detector. Each electrographic signal may be compared 915 to a threshold value for a parameter. The parameter, when varied, has a predictable effect on a detection rate of the neurological event. A rate at which the electrographic signals exceed the threshold value may be measured 920 to determine the MDR. The MDR and the TDR are then compared 925. The threshold value is then adjusted to minimize a difference between the MDR and the TDR. For example, if the MDR is greater than the TDR, the threshold value may be increased 930. If the MDR is less than the TDR, the threshold value may be decreased 935. If the MDR and the TDR are substantially similar, the threshold value may not be changed 940.

FIGS. 10A-D depict exemplary graphs of EEG activity and detection for particular detection thresholds according to an embodiment. FIGS. 10A-D illustrate the operation of a variable parameter for a particular EEG signal waveform and a detector having the following parameters: (i) the detector uses the line length data reduction methodology, (ii) the short term trend is determined over a 4096 millisecond window, (iii) the long term trend is determined over a 2 minute window, and (iv) the percentage difference for detection is varied across the figures. The percentage difference is equal to 300%, 200%, 100% and 75% for FIGS. 10A, 10B, 10C and 10D, respectively. The—axis for each figure represents time in seconds and the y-axis for each figure represents an amplitude for the EEG signal from 100% down to −100%.

As shown in FIGS. 10A-D, the areas 1001 may represent windows in which a detection event occurs. As the figure show, as the percentage difference is decreased, the detection events may occur earlier, more often and over longer periods of time. As such, more overall detections may occur and a higher MDR may result as the percentage difference decreases.

Exemplary detection parameters that may be employed in an automatic adjusting threshold detector and how adjusting such parameters based on Rx (therapy or treatment) impacts the detection rate are included below in Tables 1 and 2. Table 1 describes exemplary parameters and effects for a band pass threshold detector; Table 2 describes exemplary parameters and effects for a line length or area threshold detector. Alternate and/or additional parameters may be employed within the scope of the present disclosure. The detection system may vary the variable parameter (VP) to achieve the TDR.

TABLE 1

Band Pass Threshold Detector

| Variable Parameter | More Rx Desired | Less Rx Desired |
|---|---|---|
| Amplitude | Decrease | Increase |
| Pattern Persistence | Decrease | Increase |

TABLE 2

Line Length or Area Threshold Detector

| Variable Parameter | More Rx Desired | Less Rx Desired |
|---|---|---|
| Percentage | Decrease | Increase |

In an embodiment, the TDR may be in a range between about 1 detection event per day to about 10,000 detection events per day. Typically, the TDR is in a range between about 100 detection events per day and about 1000 detection events per day.

The variable parameter step size (VPSS) is the amount by which the VP is periodically adjusted to achieve the TDR. In an embodiment, a maximum VPSS (Max VPSS) and/or a minimum VPSS (Min VPSS) may be defined. For example, if the amount by which the VP is adjusted in a particular period is based, at least in part, on the difference between the MDR and the TDR, a VPSS from a range of VPSS values defined by the Min VPSS and the Max VPSS may be selected.

In an embodiment, a minimum variable parameter value (Min VP) and a maximum variable parameter value (Max VP) may also be defined. The Min VP and Max VP values may refer to the lowest and highest settings to which the VP may be adjusted, respectively.

An evaluation interval (EI) may also be defined. The EI is the interval at which the detection rate is calculated and compared to the TDR. Moreover, the VP may be adjusted, if necessary, based on the EI.

After an EI has elapsed, one or more actions may be performed. For example, the neurostimulation system may compare the MDR (i.e., the number of detection events over the previous EI) and compare it to a normalized TDR value. The normalized TDR value may be the stored TDR normalized to the same time base as the EI. For example, if the stored TDR is equal to 2400 detections per day and the EI is 1 hour, the normalized TDR value would be 100 detections per hour.

If the MDR is greater than the normalized TDR, the VP may be increased (made less sensitive) unless the VP is equal to the Max VP, in which case the VP would not be adjusted. In an embodiment, the VP may be increased by the VPSS if the VP is less than the Max VP. In an embodiment, the VP may be increased by a value between the Min VPSS and the Max VPSS based on the difference between the MDR and the normalized TDR if the VP is less than the Max VP. If the VP is greater than the Max VP after being increased, the VP may be set to the Max VP.

Numerous advantages may result from the use of an automatically adjusting neurological event detector as compared to a detector with a fixed threshold or thresholds. For example, use of an automatically adjusting neurological event detector may decrease the time required to tune a neurological event detector (and/or to program stimulation that the neurological event detector may also be capable of delivering) by permitting a healthcare professional to select a TDR. As such, the healthcare professional would not be required to manually adjust parameters over a series of office visits in order to achieve a target rate. This would clearly benefit the patient as well by reducing the number of office visits, co-payments and the like.

An automatically adjusting neurological event detector integrated into a neurostimulation device may also result in more uniform neurostimulation therapy distribution over time, which could provide benefit to the patient. This may result because the device may provide therapy at or near the target detection rate.

In addition, a neurological event detector with automatic threshold adjustment capability may provide a faster response to activity arising out of a quiet EEG background because the detection threshold (i.e., the VP) will be lower at such times. In other words, after an extended period of little activity on an EEG signal, the VP may be at or near the Min VP value. If activity increases on the EEG signal at the end of this period, the activity will be more likely to cause a detection event because of the small VP value.

Furthermore, a neurological event detector with an automatic threshold adjustment capability may result in more appropriately timed delivery of neurostimulation therapy during active periods than would a system in which the thresholds are fixed (at least between office visits with the clinician) because the VP at such times would be higher and situations where the detection rate exceeds the dynamic capabilities of the system to deliver neurostimulation therapy may be avoided.

A neurological event detector an automatic adjustment capability for detection thresholds may also provide more efficient battery usage when used in combination with an implantable neurostimulator, as compared to a neurostimulator that provides continuous stimulation. As such, a neurostimulator incorporating the neurological event detector described herein may be miniaturized and/or have a longer battery life than a conventional neurostimulation device.

It will be appreciated that the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A method for approximating a target detection rate for a neurological event with a neurological event detector intended for use with a human patient, comprising:
    identifying a target detection rate for the neurological event;
    monitoring electrographic signals incident on the neurological event detector;
    comparing, with a processor, each electrographic signal to a threshold value for a parameter the variation of which has a predictable effect on a detection rate of the neurological event;
    measuring a rate at which the electrographic signals exceed the threshold value to determine a measured detection rate;
    comparing the measured detection rate to the target detection rate; and
    automatically adjusting the threshold value to minimize a difference between the measured detection rate and the target detection rate based on the parameter and the predictable effect that the variation of the parameter has on the rate of detection of the neurological event.

2. The method of claim 1, wherein comparing each electrographic signal to a threshold value for a parameter the variation of which has a predictable effect on a detection rate of the neurological event includes:
    comparing each electrographic signal to a threshold value for a line length parameter which corresponds to a percentage difference between accumulated line lengths for a first electrographic signal in a window of time and accumulated line lengths for a second electrographic signal in the window of time.

3. The method of claim 1, wherein comparing each electrographic signal to a threshold value for a parameter the variation of which has a predictable effect on a detection rate of the neurological event includes:
    comparing each electrographic signal to a threshold value for a line length parameter which corresponds to a percentage difference between accumulated line lengths for an electrographic signal in a first window of time and accumulated line lengths for the electrographic signal in a second window of time.

4. The method of claim 3, wherein the accumulated line lengths for the electrographic signal in a first window of time are normalized based on a duration of the first window of time and the accumulated line lengths for the electrographic signal in the second window of time are normalized based on a duration of the second window of time.

5. The method of claim 1, wherein comparing each electrographic signal to a threshold value for a parameter the variation of which has a predictable effect on a detection rate of the neurological event includes:

comparing each electrographic signal to a threshold value for an area parameter which corresponds to the difference between an accumulated area under the curve for a first electrographic signal in a window of time and an accumulated area under the curve for a second electrographic signal in the window of time.

6. The method of claim 1, wherein comparing each electrographic signal to a threshold value for a parameter the variation of which has a predictable effect on a detection rate of the neurological event includes:

comparing each electrographic signal to a threshold value for an area parameter which corresponds to a difference between an accumulated area under the curve for an electrographic signal in a first window of time and an accumulated area under the curve for the electrographic signal in a second window of time.

7. The method of claim 6, wherein the accumulated area under the curve for an electrographic signal in the first window of time is normalized based on a duration of the first window of time and the accumulated area under the curve for an electrographic signal in the second window of time is normalized based on a duration of the second window of time.

8. The method of claim 1, wherein comparing each electrographic signal to a threshold value for a parameter the variation of which has a predictable effect on a detection rate of the neurological event includes:

comparing each electrographic signal to one or more of an amplitude threshold and a persistence threshold.

9. The method of claim 1, wherein the target detection rate is expressed as a number of neurological events per unit of time.

10. The method of claim 1, wherein automatically adjusting the threshold value to minimize a difference between the measured detection rate and the target detection rate based on the parameter and the predictable effect that the variation of the parameter has on the rate of detection of the neurological event includes:

decreasing the threshold value when the measured detection rate is less than the target detection rate.

11. The method of claim 1, wherein automatically adjusting the threshold value to minimize a difference between the measured detection rate and the target detection rate based on the parameter and the predictable effect that the variation of the parameter has on the rate of detection of the neurological event includes increasing the threshold value when the measured detection rate is greater than the target detection rate.

12. The method of claim 1, wherein the neurological event is selected from the group consisting of epileptiform activity characteristic of an onset of a seizure, epileptiform activity characteristic of an occurrence of a seizure, electrocortical signals predictive of a tic disorder, electrographic signals characteristic of an occurrence of a symptom of a tic disorder, electrocortical signals predictive of a movement disorder, electrographic signals characteristic of an occurrence of a symptom of a movement disorder; electrocortical signals predictive of a sleep disorder, electrographic signals characteristic of an occurrence of a sleep disorder, electrocortical signals predictive of a mood disorder, electrographic signals characteristic of an occurrence of a symptom of a mood disorder, and electrocortical signals predictive of an anxiety disorder, electrographic signals characteristic of an occurrence of a symptom of an anxiety disorder.

13. The method of claim 1 wherein the predictable effect that the variation of the parameter has on the rate of detection of the neurological event is to increase or decrease a sensitivity of the neurological event detector.

14. In a neurological event detector intended for use with a human patient, a method for minimizing the difference between a target detection rate and a measured detection rate for a neurological event, comprising:

identifying a target detection rate for the neurological event;

monitoring electrographic signals sensed from the human patient by the neurological event detector;

comparing, with a processor, each electrographic signal to a threshold value for a parameter the variation of which has a known relationship to a sensitivity of the neurological event detector to register a detection of the neurological event;

measuring a rate at which the electrographic signals exceed the threshold value to determine a measured detection rate;

comparing the measured detection rate to the target detection rate; and automatically adjusting the threshold value to minimize a difference between the measured detection rate and the target detection rate based on the parameter and the known relationship that the variation of the parameter has on the sensitivity of the neurological event detector to register a detection of the neurological event.

15. The method of claim 14, wherein automatically adjusting the threshold value to minimize a difference between the measured detection rate and the target detection rate based on the parameter and the known relationship that the variation of the parameter has on the sensitivity of the neurological event detector to register a detection of the neurological event includes:

decreasing the threshold value when the measured detection rate is less than the target detection rate.

16. The method of claim 14, wherein automatically adjusting the threshold value to minimize a difference between the measured detection rate and the target detection rate based on the parameter and the known relationship of the variation of the parameter to a sensitivity of the neurological event detector to register a detection of the neurological event includes:

increasing the threshold value when the measured detection rate is greater than the target detection rate.

17. A neurological event detector intended for use with a human patient to detect a neurological event, comprising:

at least one sensor configured to receive electrographic signals from the human patient;

a detector configured to analyze the electrographic signals to identify an occurrence of the neurological event whenever a threshold value for a parameter is exceeded, wherein variation of the parameter has a predictable effect on a detection rate of the neurological event, wherein an output of the detector is a measured detection rate;

a memory configured to store a target detection rate and from which the target detection rate is accessible;

a comparator configured to compare the measured detection rate to the target detection rate; and a parameter adjuster configured to automatically adjust the threshold value to minimize a difference between the measured detection rate and the target detection rate based on the parameter and the predictable effect that the variation of the parameter has on the rate of detection of the neurological event.

18. The neurological event detector of claim 17, wherein the parameter is a difference in line length between accumulated line lengths for a first electrographic signal in a window of time and accumulated line lengths for a second electrographic signal in the window of time.

19. The neurological event detector of claim 17, wherein the parameter is a difference in line length between accumulated line lengths for an electrographic signal in a first window of time and accumulated line lengths for the electrographic signal in a second window of time.

20. The neurological event detector of claim 19, wherein the accumulated line lengths for the electrographic signal in the first window of time are normalized based on a duration of the first window of time and the accumulated line lengths for the electrographic signal in the second window of time are normalized based on a duration of the second window of time.

21. The neurological event detector of claim 17, wherein the parameter is a difference in area between accumulated area under the curve for a first electrographic signal in a window of time and accumulated area under the curve for a second electrographic signal in the window of time.

22. The neurological event detector of claim 17, wherein the parameter is a difference in area between accumulated area under the curve for an electrographic signal in a first window of time and accumulated area under the curve for the electrographic signal in a second window of time.

23. The neurological event detector of claim 22, wherein the accumulated area under the curve for the electrographic signal in the first window of time is normalized based on a duration of the first window of time and the accumulated area under the curve for the electrographic signal in the second window of time is normalized based on a duration of the second window of time.

24. The neurological event detector of claim 17, wherein the parameter is one or more of an amplitude threshold and a persistence threshold.

* * * * *